US008852875B2

(12) United States Patent
Toner et al.

(10) Patent No.: US 8,852,875 B2
(45) Date of Patent: Oct. 7, 2014

(54) METHODS FOR COUNTING CELLS

(75) Inventors: Mehmet Toner, Wellesley, MA (US);
Rashid Bashir, Champaign, IL (US);
Xuanhong Cheng, Charlestown, MA
(US); Utkan Demirci, Cambridge, MA
(US); Daniel Irimia, Charlestown, MA
(US); William R. Rodriguez,
Cambridge, MA (US); Liju Yang, Apex,
NC (US); Lee Zamir, Cambridge, MA
(US); Yi-Shao Liu, Champaign, IL (US)

(73) Assignees: The General Hospital Corporation,
Boston, MA (US); **Purdue Research
Foundation**, West Lafayette, IN (US)

( * ) Notice: Subject to any disclaimer, the term of this patent is extended or adjusted under 35 U.S.C. 154(b) by 737 days.

(21) Appl. No.: 12/596,768

(22) PCT Filed: Apr. 21, 2008

(86) PCT No.: PCT/US2008/005066
§ 371 (c)(1),
(2), (4) Date: Aug. 3, 2010

(87) PCT Pub. No.: WO2008/130655
PCT Pub. Date: Oct. 30, 2008

(65) Prior Publication Data
US 2012/0003687 A1    Jan. 5, 2012

Related U.S. Application Data

(60) Provisional application No. 60/925,368, filed on Apr. 20, 2007.

(51) Int. Cl.
*G01N 33/567* (2006.01)
*G01N 33/50* (2006.01)
*G01N 33/84* (2006.01)
*G01N 15/10* (2006.01)
*G01N 15/14* (2006.01)

(52) U.S. Cl.
CPC ........ *G01N 33/5005* (2013.01); *G01N 15/1056* (2013.01); *G01N 2015/1062* (2013.01); *G01N 33/84* (2013.01); *G01N 2015/1006* (2013.01); *G01N 15/1484* (2013.01); *G01N 15/1031* (2013.01)
USPC ...................................................... 435/7.21

(58) Field of Classification Search
USPC ........................................................ 435/7.21
See application file for complete search history.

(56) References Cited

U.S. PATENT DOCUMENTS

| 5,964,096 | A | 10/1999 | Watson et al. |
| 6,472,215 | B1 * | 10/2002 | Huo et al. .................... 436/10 |
| 6,641,708 | B1 * | 11/2003 | Becker et al. ................ 204/547 |
| 7,257,279 | B2 | 8/2007 | Guo et al. |
| 2003/0170613 | A1 | 9/2003 | Straus |
| 2005/0239046 | A1 | 10/2005 | Sachs et al. |
| 2006/0175192 | A1 | 8/2006 | Lin |
| 2006/0177347 | A1 | 8/2006 | Larsen |
| 2007/0026381 | A1 * | 2/2007 | Huang et al. .................. 435/4 |
| 2007/0196820 | A1 | 8/2007 | Kapur et al. |
| 2008/0261262 | A1 * | 10/2008 | Godfrin ....................... 435/30 |

FOREIGN PATENT DOCUMENTS

| EP | 0 713 087 | 4/1999 |
| EP | 1701150 A1 | 9/2006 |
| WO | WO 93/01306 A1 | 1/1993 |
| WO | WO 01/18246 | 3/2001 |
| WO | WO 03048728 A2 | 6/2003 |
| WO | WO 2007008223 A2 | 1/2007 |

OTHER PUBLICATIONS

Suehiro et al. (High sensitive detection of biological cells using dielectrophoretic impedance measurement method combined with electropermeabilizatiion, 2003, Sensors and Actuators B, vol. 96, pp. 144-151).*
van der Werf et al. (Permeabilization and lysis of *Pseudomonas pseudoalcaligenes* cells by Triton-X-100 for efficient production of D-malate, 1995, Appl Microbiol Biotechnol, vol. 43, pp. 590-594).*
Mishra et al. (On-chip micro-biosensor for the detection of human CD4+ cells based on AC impedance and optical analysis, 2005, Biosensors and Bioelectronics, vol. 21, pp. 696-704).*
International Search Report for PCT/US08/05066.
Allen et al., "Lactate dehydrogenase activity as a rapid and sensitive test for the quantification of cell numbers in vitro," Clinical Materials, Elsevier, vol. 16, No. 4, Jan. 1, 1994, pp. 189-194.
"Impedance Microbiology-on-a-Chip: Microfluidic Bioprocessor for Rapid Detection of Bacterial Metabolism," Journal of Microelectromechanical Systems, IEEE Service Center, Piscataway, NJ, US, vol. 14, No. 4, Aug. 1, 2005, pp. 829-838, Gomez-Sjoberg et al.
Cheng, Xuanhong et al., "Cell detection and counting through cell lysate impedance, spectroscopy in microfluidic devices," Lab on a Chip, Royal Society of Chemistry, vol. 7, No. 6, Jun. 1, 2007, pp. 746-755.
Jönsson, Mats et al., "Bacteria counting with impedance spectroscopy in a micro probe station," The Journal of Physical Chemistry. May 25, 2006, vol. 110, No. 20, 25, pp. 10165-10169.
Soley et al., "On-line monitoring of yeast cell growth by impedance spectroscopy," Journal of Biotechnology, Elsevier Science Publishers, Amsterdam, NL, vol. 118, No. 4, Sep. 10, 2005, pp. 398-405.
Wang et al., "A microfluidic flow-through device for high throughput electrical lysis of bacterial cells based on continuous dc voltage," Biosensors and Bioelectronics, Elsevier BV, NL, vol. 22, No. 5, Dec. 15, 2006, pp. 582-588.

(Continued)

*Primary Examiner* — Bin Shen
(74) *Attorney, Agent, or Firm* — Fish & Richardson P.C.

(57) ABSTRACT

The invention features methods of quantifying cells in a sample by lysing the cells followed by the measurement of at least one intracellular component. Methods of the invention are especially useful for quantifying small numbers of cells, e.g., over a large surface area or volume compared to the cell size. In a preferred embodiment, methods of the invention are performed using a microfluidic device.

16 Claims, 6 Drawing Sheets

(56) References Cited

OTHER PUBLICATIONS

European Search Report mailed Mar. 17, 2011 in corresponding European application serial No. 08743095.5.

Singapore Written Opinion (9 pages) and Singapore Search Report (9 pages) from the Danish Patent and Trademark Office dated Jan. 11, 2011.

Office Action issued in Australian Application No. 2008241388 dated Apr. 26, 2012, 2 pages.

Office Action issued in Chinese Application No. 200880020891 dated Jul. 17, 2012, 25 pages.

Written Opinion issued in International Application No. PCT/US08/05066 dated Jul. 17, 2008, 3 pages.

Examination Report from corresponding Singapore application, 201202915-3, dated Jul. 25, 2014 (4 pages).

* cited by examiner

METHODS FOR COUNTING CELLS

CROSS-REFERENCE TO RELATED APPLICATIONS

This application claims benefit of International Application No. PCT/US2008/005066, filed Apr. 21, 2008, and U.S. Provisional Application No. 60/925,368, filed Apr. 20, 2007, both of which are incorporated herein by reference in their entirety.

BACKGROUND OF THE INVENTION

This invention relates to the fields of medical devices, medical diagnostics, and cell counting.

Microfluidic systems have shown unique promise for studying cell function, cell and tissue engineering, disease diagnosis, blood sample preparation, and drug discovery. Very recently, the use of microfluidics to isolate pure populations of leukocyte subsets from whole blood has attracted a lot of interest for point-of-care diagnositics. While the principle behind a cell isolation approach can be easily adapted to a wide spectrum of clinical applications, detecting these isolated cells remains a technical challenge to be addressed.

The use of optical microscopy for detection and quantification of surface immobilized cells within microdevivces does not represent the optimal solution for point-of-care applications. This is because optical detection methods depend on a stable light path, lensing, filtering, and focusing mechanisms that could add cost and complexity to detection. In addition, optical detection tends to be low throughput, because of the small detection area available at a single time. At the same time, the most commonly used cell counting strategies like flow cytometry and impedance measurement (i.e., Coulter counters) cannot be applied to cells attached on surfaces, despite miniaturized platforms having been implemented by several researchers. Alternative techniques to detect attached cells by substrate impedance sensing require cell coverage on the electrode surface to reach near unity for detectable measurements. Studies using non-optical methods to detect few cells on large surface areas in a relatively large volume—including even the microliter volumes of microscale devices have not yet been reported, despite the need for non-optical detection methods in microfluidic applications.

Detection and enumeration of cells are essential for medical diagnostics, especially AIDS, cancer diagnosis, and pathogen detection. While most existing methods to detect cells are optical (i.e., microscopy), electrical detection is significantly simpler, cheaper, and more amenable to point of care devices. To date, electrical detection and enumeration of intact cells based on impedance spectroscopy (i.e., detection of changes in electrical impedance caused by the presence of cells) have proven to be extremely practical and inexpensive, but limited to large cell populations or homogenous cell types (e.g., Coulter counting of red blood cells).

SUMMARY OF THE INVENTION

In one aspect, the invention features a method of counting cells (e.g., mammalian, fungal, protist, or bacterial cells) in a sample by introducing the sample into a channel, lysing the cells in the channel, and measuring at least one property of at least one cellular component resulting from the lysing. In this aspect, the cellular component is indicative of the number of cells lysed in the channel.

In another aspect, the invention features a method of counting cells (e.g., a mammalian, fungal, protest, or bacterial cell) in a sample including the steps of introducing the sample into a channel (e.g., a microfluidic channel), introducing a non-conductive solution into the channel (e.g., a sugar solution), applying an electric field to the channel, measuring the impedance of the channel, replacing the non-conductive solution with a lysing non-conductive solution (e.g., a detergent solution) and allowing at least one cell to lyse, applying an electric field to the channel, and measuring the impedance of the channel. In this aspect a decrease in the impedance after lysis is indicative of the number of the cells in the sample. In this aspect, the impedance is measured, for example, using a top down electrode, IDT electrode, or a two rail electrode. Desirably, the impedance of the non-conductive solution prior to lysis is greater than 1,000 ohms, greater than 10,000 ohms, greater than 100,000 ohms, greater than 1,000,000 ohms or greater.

In another aspect, the invention features a method of diagnosing a condition in a subject by introducing a sample (e.g., a human blood sample) containing a population of cells (e.g., CD4 helper cells) into a channel, lysing the population of cells in the channel, and measuring at least one property of at least one cellular component resulting from the lysing. In this aspect, the cellular component is indicative of the number of cells lysed in the channel and the number of cells is diagnostic for the condition.

In another aspect, the invention features a kit for counting cells including a device, a non-conductive solution (e.g., a sugar solution), and a lysing non-conductive solution (e.g., a detergent solution). In this aspect, the device includes a microfluidic channel and an electrode (e.g., top down electrode, IDT electrode, and a two rail electrode) to measure the impedance of the microfluidic channel. In any of the forging aspects, the detergent can be triton-X or tween-20.

In any of the forgoing aspects, the cellular component can be an ion (e.g., potassium, calcium, and sodium) or an enzyme (e.g., lactate dehydrogenase).

In any of the forgoing aspects, the property resulting from the lysing can be impedance. In this aspect, the impedance can be measured using a top down electrode, IDT electrode, and a two rail electrode.

In any of the forgoing aspects, impedance can be, for example, measured using a single frequency (e.g., 760 Hz) or using an ion sensitive electrode (e.g., a potassium, sodium or calcium ion-specific electrode).

Alternatively, the property resulting from lysing can be mass. In this aspect, the mass can be measured using a micro- or nano-mechanical resonator.

In any of the forgoing aspects, the measuring can include optical detection, surface plasmon resonance, or a lateral flow diffusion assay.

In one preferred embodiment, the property is measured using fluorescent probes and the ion is potassium. In another preferred embodiment, the cellular component is a nucleus, and the property resulting from the lysing is impedance. In yet another preferred embodiment, the microfluidic channel has a volume of 10 µl.

In any of the above methods, the population of cells and the condition can be selected from Table 1.

TABLE 1

| Cell Population | Condition |
| --- | --- |
| Neutrophil | Effects of Immunosuppressive drug treatment |
| Monocyte | Differential blood count |

TABLE 1-continued

| Cell Population | Condition |
| --- | --- |
| Lymphocyte | AIDS |
| Lymphocyte | Effects of Immunosuppressive drug treatment |
| Lymphocyte B | Immune response to infection |
| Circulating tumor cells | Cancer |
| Dendritic cells | Immune responses |
| Red blood cells | Malaria |
| Tuberculosis sensitive CD8 T cell | Latent tuberculosis |
| Platelets | Effects of anti-thrombotic drug treatment |
| Endothelial progenitor cells | Health status of vasculature |
| Lymphocyte | Meningitis |
| Lymphocyte | Urinary tract infection |

By "lysis" is meant disruption of the cellular membrane (e.g., the membrane of plant cells, animal cells, and bacterial cells). For the purposes of this invention, the term "lysis" is meant to include complete disruption of the cellular membrane ("complete lysis"), incomplete disruption of the cellular membrane ("partial lysis"), and permeabilization of the cellular membrane. The term "lysis" is also meant to include the disruption of other biological membranes, (e.g., nuclear membranes and mitochondrial membranes).

By "selective lysis" is meant the application of a reagent to a heterogenous population of cells (e.g., a human blood sample) such that a subpopulation of desired cells is lysed while the undesired cells remain intact.

By "permeabilization" is meant the disruption of the cellular membrane such that certain intracellular components to which the membrane is not normally permeable to the same extent, are able to escape the cell, while other components remain inside the cell.

By "cellular component" is meant any chemical species or complex found within or on a cell. For the purposes of this invention, this term is meant to include biological compounds or complexes (e.g., enzymes, nucleic acids, proteins, organelles, and cell membrane complexes), as well as other species (e.g., ions and organic molecules).

By "property of at least one cellular component" is meant a measurable feature of a particular cellular component.

DETAILED DESCRIPTION OF THE INVENTION

Figure 1:
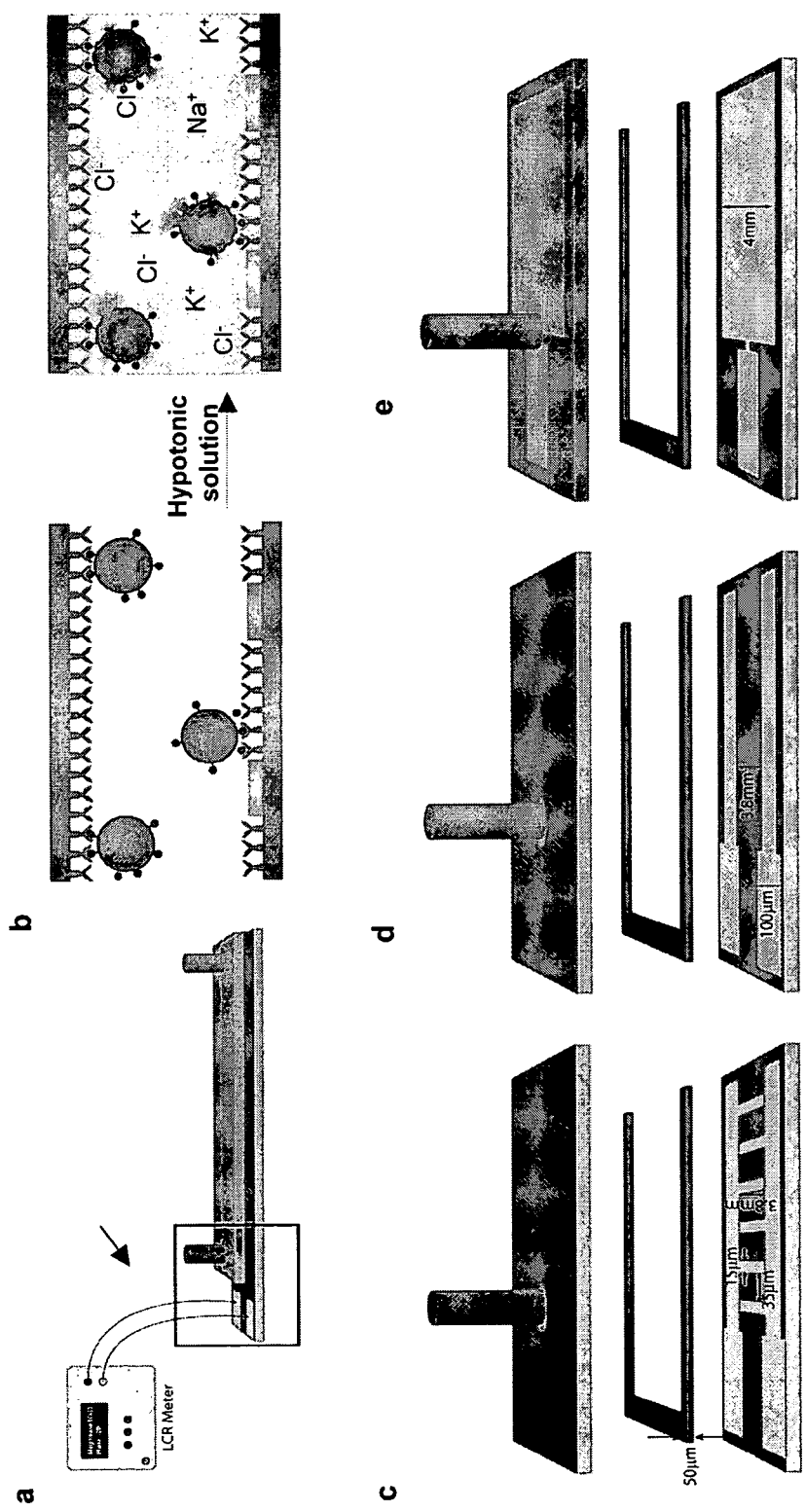
FIG. 1A is a schema showing an impedance measurement setup. Samples were delivered into the micro-channels through an inlet (arrow) via a syringe pump.
FIG. 1B is an illustration showing measurement of cell ion release using impedance spectroscopy. Target cells isolated within a microfluidic device are lysed to release intracellular ions. This leads to the increase of bulk conductance change, which can be monitored using surface patterned electrodes and impedance spectroscopy to detect cell numbers.
FIG. 1C-FIG. 1E are schematics showing details of the electrode layout and device assembly: (C) interdigitated (IDT) co-planar electrodes, (D) simple two-rail co-planar electrodes and (E) top-bottom electrodes. The electrodes were patterned either on the bottom slides (for the IDT and two rail electrode designs) or on both slides (for the top-bottom electrode design) using standard cleanroom techniques and gold wet etching processes. All devices were made by bonding two pieces of glass slides to 50 μm-thick PDMS gaskets (triangle). Holes were drilled on the cover slides and assembled with PDMS ports to serve as sample inlets and outlets

In general, the invention features methods of quantifying cells or components thereof in a sample by lysing the cells followed by the measurement of at least one cellular component. Methods of the invention are especially useful for quantifying small numbers of cells, e.g., over a large surface area or volume compared to the cell size. In a preferred embodiment, methods of the invention are performed in a microfluidic device.

In aspects of the invention where quantification of one or more sub-populations of cells within a heterogenous mixture of cells (e.g., from a human blood sample) is desired, the invention features the selective lysis of the desired cell subpopulation. Alternatively, or additionally, the invention features the isolation of one or more of the desired sub-populations of cells prior to lysis. In this aspect, the desired cell population(s) can be captured in a small volume in the microfluidic device. In these embodiments, only the desired subpopulation is lysed and quantified.

I. Methods of Lysing Cells

Methods of lysis of the invention include complete lysis, partial lysis, selective lysis, and permeabilization of the cells. In one embodiment the methods of lysis include chemical lysis (e.g., with hypotonic solutions) or lysis or partial lysis using detergents such as triton-X, tween-20 and other commercially available detergents, and subsequent analysis of the lysate for counting of cells or components thereof.

In another embodiment, methods of the invention feature electrical lysis (e.g., by applying a direct current, alternating current, or pulsed electric field sufficient to cause cell lysing) and subsequent analysis of the lysate for counting of cells. Electrical lysing can be accomplished by electrodes built into the chip for measurement of impedance (e.g., see below), or can be performed with an additional set of electrodes, for example on the surface opposing the electrodes built for measurement of impedance.

In another embodiment, the invention features mechanical lysing and subsequent analysis of the lysate for counting of cells. Methods of mechanical lysis include applying ultrasonic waves to the cells, freezing and thawing the cells, heating the cells, on chip homogenization of the cells using micro or nano-scale needles, sharp probes, edges and ridges, and other means known in the art.

The invention can also feature lysis that is biological in nature. For example lysis can be the result of infection with a lytic virus, the result of interaction with immune system components (e.g., exposure to complement), or the result of interaction with pore forming biological molecules (e.g., porins)

The invention also features specific lysis of subpopulation of cells within a heterogeneous mixture of cells. In this aspect, reagents which induce lysis can be linked to binding moieties that specifically bind to a cell surface marker on the desired sub-population of cells. Alternatively, lysing reagents may be introduced at a concentration or magnitude sufficient to lyse a desired subpopulation of cells, but insufficient to lyse the remaining undesired cells. Other methods of lysing are known in the art.

II. Methods of Measuring Cellular Contents

The invention features methods of quantifying cells by measuring the intracellular contents released by cellular lysis. Methods of the invention may be fully quantitative, semi-quantitative, or qualitative, depending on the desired accuracy.

A. Electrical

The invention features electrical methods for measuring the intracellular contents of cells. In one embodiment, cells in a sample are rinsed with an isotonic, non-conductive solution (e.g., 8.5% sucrose). Cells remain intact while the conductivity of the surrounding medium decreases substantially, and measured impedance increases. Next, a hypotonic, non-conductive solution (e.g., 2% sucrose) is added, lysing the cells. The release of intracellular ions from the cells into the medium leads to an increase in conductivity, and a measurable decrease in impedance. Because substantially all ions now present in the medium are from the cells, the absolute number of cells can be determined based on the measured impedance. A-priori or subsequent measurements of known reference solutions in the same device can be used for calibration of each measurement.

In another embodiment, the invention features the use of a mild detergent to release intact cell nuclei. The number of nuclei may be counted using a micro-coulter counter. A coulter counter works by measuring the change in impedance as particles pass through an aperture in a conductive medium.

In another embodiment, the invention features the use of ion sensitive electrodes or microelectrodes to detect the concentration of specific ions (e.g., potassium, sodium, or calcium), and the concentration of ions in the lysate can be correlated to the number of cells captured.

B. Optical

The invention also features optical methods for measuring the intracellular contents of cells, preferably on a microfluidic device. In one embodiment, the invention features a semi-quantitative colorimetric method based on measurement of the activity of cytosolic enzymes. One example in this category is a lactate dehydrogenase (LDH) assay, which measures activity of a cytoplasmic enzyme, LDH, after its release from a cell. This embodiment may involve lysis of immobilized cells (e.g., an enriched population) with surfactant to release LDH, followed with mixing the lysate with an enzymatic solution that changes color upon reaction with LDH. Optical absorbance of the final solution is mapped onto a standard curve obtained using lysate of known cell concentrations to estimate the number of lysed cells.

In another embodiment, the invention features semi-quantitative spectroscopic methods using surface plasmon resonance (SPR). In this embodiment, a specific component, such as a protein in the lysate can be captured onto a metal surface using a specific antibody, or other capture moiety, and the captured mass can be quantified using SPR spectroscopy. In another embodiment, the invention features oligonucleotide-based fluorescent probes for detection of potassium ions in the lysate solution. The fluorescence signal can be correlated to the number of cells.

In another embodiment, the invention features capillary ion electrophoresis on cell lysates. This method can be used in combination with a measurement of UV absorbance to determine the presence of specific ions that correlate to the concentration of cells.

In another embodiment, the invention features a lateral flow diffusion based assay. In this method, the number of cells is determined based on the diffusion of the molecular contents in the cellular lysate. Strips of molecules can be patterned that recognize and bind to target molecules in the cell lysate. The lysate can be introduced in the lateral flow device and the distance traveled by the target molecules at a certain concentration threshold can be correlated to the number of cells in the original sample.

C. Mechanical

The invention features mechanical methods for quantifying the intracellular contents of cells. Mass is a fundamental property that can be used to quantify cell number. In this embodiment, a cell lysate can be dried and weighed using micro- and nano-mechanical resonators that allow measurement of mass down to the attogram range. Alternatively, a specific lysate component can be captured and weighed, for example, using an antibody-functionalized (or other capture moiety) cantilever. The mass of specific proteins can be then be correlated to the number of cells in the lysate.

III. Indications

The methods described herein can broadly be used for automated detection and counting of any cell population. The methods are useful for detection and counting of all cells in a sample, or cells which are isolated from the remaining cells of a sample. The invention is especially suited for automating the detection and quantification of relatively low concentrations of cells, for example, 100 to 1000 cells per milliliter. In one embodiment, the invention features the counting of CD4+ cells from a sample of blood. The invention can also be used, for example, for counting of rare epithelial cancer cells from blood, counting of cells expressing specific antigenic receptors on their surface indicating disease, counting of target neutrophils from blood, counting of specific monocytes from blood, and counting of cells in other body fluids such as urine, cerebrospinal fluid, saliva, and sputum.

In some methods of the invention, quantification of cells possessing certain cell surface antigens is useful for diagnosing or assessing certain medical conditions. Cells can be first captured using binding moieties specific for desired cell surface antigens and then quantified using any of the above methods. Table 2 sets forth an exemplary list of applications where specific cell count is desired for a variety of medical and clinical diagnostics. Table 2 also sets forth exemplary capture molecules that can be used to isolate the indicated cell population.

TABLE 2

| Cell population | Capture molecule | Application |
| --- | --- | --- |
| Neutrophil | Anti-CD66 | Differential blood count, monitoring of immunosuppressive drug treatment |
| Monocyte | Anti-CD14 | Differential blood count |
| Lymphocyte | Anti-CD4 | AIDS monitoring |
| Lymphocyte | Anti-CD8 | Ratio of CD4/CD8 numbers for monitoring pediatric AIDS |
| Lymphocyte | Anti-CD45 | Immunosuppressive drug treatment |
| Lymphocyte B | Anti-CD19 | Monitoring immune response to infection |
| Circulating tumor cells | Anti- EPCAM | Cancer monitoring |
| Dendritic cells | Anti-CD83 | Monitoring immune responses-general |
| Red blood cells | Anti-Apical membrane antigen 1 (AMA-1) | Malaria diagnostic |
| Red blood cells | Anti-PfEMP1 (parasite-derived proteins) | Malaria diagnostic |
| Tuberculosis sensitive CD8 T cell | Anti-P MHC Pentamer A2-SL9 | Diagnostic of latent tuberculosis |
| Platelets | Anti-CD41 | Monitoring anti-thrombotic drug treatment |
| Endothelial progenitor cells | Anti-CD34 | Monitoring health status of vasculature |
| Lymphocyte | Anti-CD3 | Total Lymphocyte count in cerebrospinal fluid for meningitis diagnostic/monitoring and total lymphocyte count in urine for urinary tract infection diagnostic/monitoring |

In addition, it should be noted that combination of cell counts would be useful for a variety of medical applications. These could include (i) differential blood count—including neutrophils, lymphocytes, monocytes, and platelets, (ii) pediatric AIDS diagnostic (e.g., ratio of CD4 to CD8), (iii) malaria (panel of PfEMPs (parasite derived proteins)), (iv) monocytes and Lymphocytes for monitoring and differentiating viral and bacterial infections. In addition, this invention encompasses any cell count where specific cells are captured alone or in combinations.

IV. Examples

To address the need to detect a small number of cells immobilized on a relatively large surface area or in a large volume, we investigated the release of intracellular ions from lysed cells immobilized in a microfluidic channel, using surface-patterned electrodes to measure bulk conductance changes through impedance spectroscopy. Mammalian cells contain a significant amount of ions, and tight control of ion transport across cell membranes is central to normal cell function and response to the surrounding environments. When cells are suspended in hypotonic media, passive diffusion and active pumping of intracellular ions to the extracellular milieu are used to adjust to the hypoosmotic environment. Here, we show that by controlled release of intracellular ions, we can perform impedance measurements to determine the number of cells present in a microfluidic channel. Using captured and immobilized CD4 T cells as an example, following our previous success in separating these cells from whole blood, we demonstrate that cell lysate impedance spectroscopy has a detection threshold of 20 cells per µL, which is sufficiently useful for clinical and research applications.

Modeling of Cell Ion Release-Based Impedance Spectroscopy

Conductance Vs. Capacitance Change Due to Ion Release

When cells release ions, both bulk conductance and capacitance are affected. In a typical mammalian cell, cytoplasmic ion concentration is roughly 150 mM (Aidley, et al., Ion Channels: Molecules in Action, Cambridge University Press, Cambridge, UK, 1996.). Given a volume of 0.2 pL, a typical lymphocyte therefore contains a total of $3 \times 10^{-14}$ molar ions. After lysis in a 10 µL micro-chamber (the volume of the microfluidic device used in this study), these ions contribute a 3 nM increase of ionic concentration. Thus, for every 100 lymphocytes, complete lysis in a 10 µL chamber would increase the solution ionic concentration by 0.3 µM. If we simplify the situation by assuming all released ions are potassium and chloride ions, and that potassium and sodium ions have comparable electrical mobility (Ohno, ed., Electrochemical Aspects of Ionic Liquids, Wiley-Interscience, c2005, Hoboken, N.J., 2005.), the solution conductivity can be calculated to increase by 0.03/MΩ-cm from an increase of 0.3 μM in ionic concentration (Omega Engineering, Technical Conductivity and Resistivity. Accessed: Dec. 30, 2006.). This conductivity change is more than 50% of the increase seen with deionised water (0.055/MΩ-cm). In comparison, capacitance depends only weakly on ionic concentration in a dilute solution. For a sodium chloride solution, for example, dielectric constant drops by only $10^{-7}$ for every nanomole increase in ion concentration in a dilute solution (<100 mM). Using a similar calculation, the total ions released from 100 lymphocytes only reduces the solution capacitance by $4 \times 10^{-7}$ relative to deionised water (dielectric constant of 80). This change is several orders of magnitude lower than the change in bulk conductance. Thus, cell ion release mainly contributes to solution conductance change, which can be easily detected using impedance spectroscopy.

Modeling of Impedance Spectra

Figure 3:
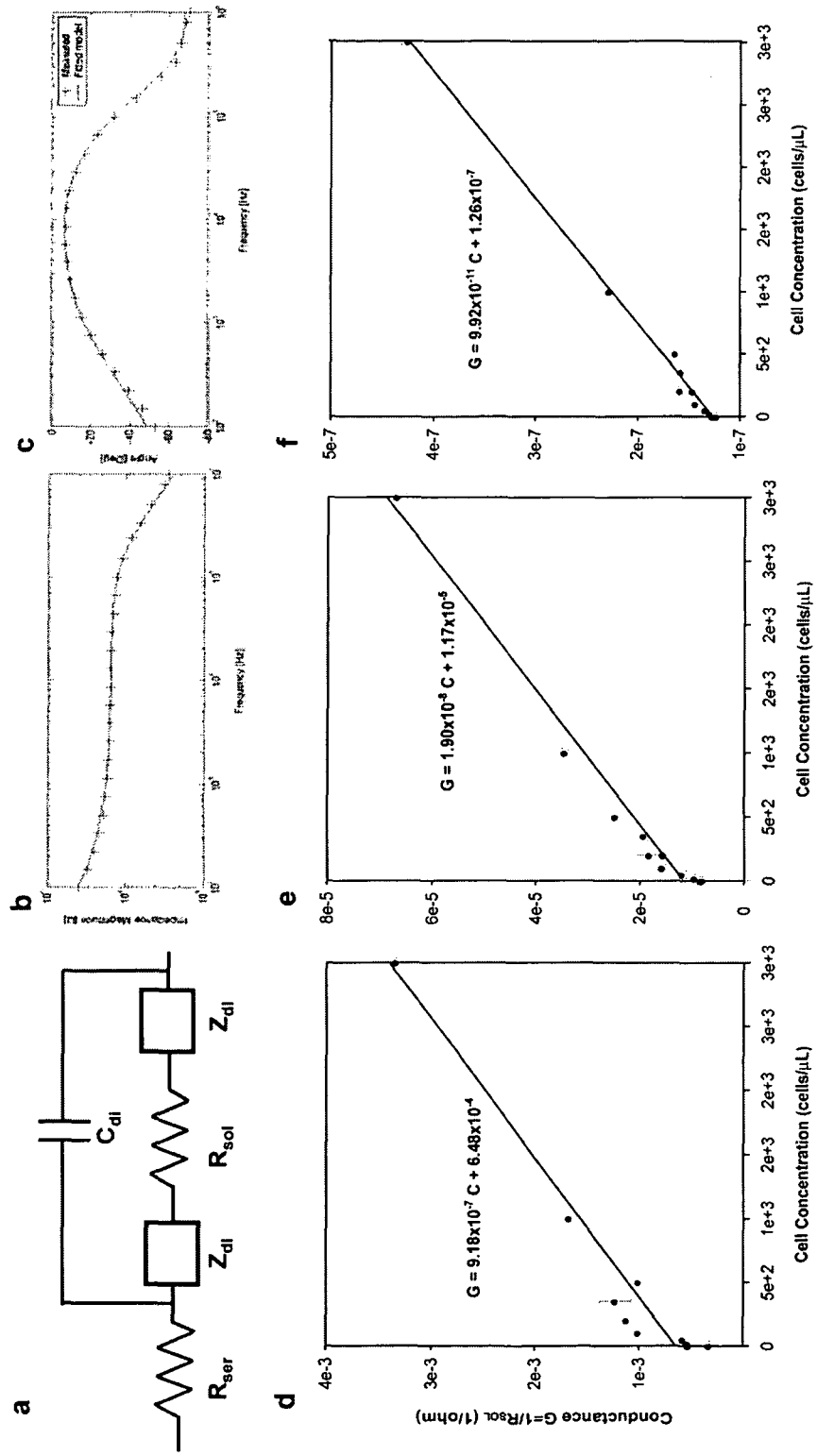
FIG. 3A is a schematic showing a circuit model for fitting of the impedance spectra and extracted conductance as a function of cell concentration. An equivalent circuit used in our study to model the electrode/electrolyte system for extracting bulk solution conductance, $R_{sol}$, which directly correlates with cell ion release.
FIGS. 3B and 3C are graphs showing impedance magnitude (B) and phase (C) spectra plotted using off-chip cell lysate sample with a cell concentration of 3000 cells/mL in the IDT electrode chip. Crosses are the experimental data and solid lines show the fitting curves.
FIG. 3D-3F are graphs showing bulk conductance. $R_{sol}$ is extracted from spectra measured using (D) top-bottom electrodes, (E) IDT electrodes and (F) two-rail electrodes. Linear relationships between measured bulk solution conductance (solid dots) and cell concentration are observed using all electrode geometries, and the best fits are shown as solid lines and equations in (D)-(F). Error bars in (D)-(F) indicates the standard deviation from 3-5 continuous measurements within a single device.

To understand solution conductance as a function of cell number, we carried out modeling studies to extract bulk conductance in microfluidic devices from impedance spectra obtained using surface patterned electrodes. Electrodes in a electrolyte solution can be modeled using an equivalent circuit as shown in FIG. 3A (Gomez-Sjoberg, et al., J. Microelectromech. Syst., 2005, 14, 829-838. Gomez, et al., Sens. Actuator B-Chem., 2002, 86, 198-208.), where $C_{di}$ is the dielectric capacitance (it contains dielectric contributions from all the materials surrounding the electrodes, including the solution), $R_{sol}$ is the bulk solution resistance (charge transport across the bulk solution), $Z_{di}$ is the interfacial impedance (the so-called Warburg impedance), which accounts for the change in the ionic gradient at the interface, and $R_{ser}$ is resistance of the on-chip wiring. The interfacial impedance can be expressed as $$Z_{di}=1/[(j\overline{\omega})^n B] \quad (1),$$

Where $j=\sqrt{(-1)}$, n and B are parameters dependent on the properties of the electrolytes and of the electrodes. This is the simplest model that would properly fit the measured data over the whole frequency range at all times.

Materials and Methods

Chemicals

Sucrose was purchased from Mallinckrodt Baker, Inc. (Paris, Ky.). Dextrose and Trypan blue solution (0.4%) were purchased from Sigma-Aldrich (St. Louis, Mo.). Ficoll-Paque Plus was purchased from GE Healthcare Amersham Biosciences Corp (Piscataway, N.J.). 3-Mercaptopropyl trimethoxysilane was purchased from Gelest (Morrisville, Pa.). Gold slides were obtained from Fisher Scientific (Fair Lawn, N.J.). Phosphate buffered saline (PBS) was obtained from Mediatech (Herndon, Va.). Lyophilized bovine serum albumin (BSA) was obtained from Aldrich Chemical Co. (Milwaukee, Wis.). The coupling agents GMBS (N-γ-maleimidobutyryloxy succinimide ester) and NeutrAvidin were obtained from Pierce Biotechnology (Rockford, Ill.). Biotinylated mouse anti-human anti-CD4 (clone 13b8.2) was purchased from Beckman Coulter (Somerset, N.J.).

Devices

Three type of devices were fabricated, implementing three different electrode designs, including interdigitated (IDT) co-planar electrodes, simple two-rail co-planar electrodes, and top- and bottom-electrodes (FIGS. 1C-D). The gold electrodes were constructed using standard photolithography and gold wet etching processes. The IDT electrode fingers were 3.8 mm×15 μm, with spacing of 35 μm. They covered the entire area within the microfluidic channel and were broken into three identical segments to probe different sections of the chamber. The connecting rails for the IDT electrodes and the rails of the simple two-rail electrodes were 100 μm wide with spacing of 3.8 mm. The top-bottom electrodes were 5 cm×4 mm gold pads.

For all devices, the top and bottom slides (75 mm×25 mm) were bonded to 50 μm thick PDMS gaskets with an opening of 5 cm×4 mm, forming closed microfluidic channels. The PDMS gaskets were prepared by spin-coating PDMS on transparency slides, followed by hand-cutting windows of desired size. Two holes were drilled on the top glass and assembled with PDMS ports to form fluid inlets and outlets. Devices employed to measure impedance from off-chip lysates were used directly after assembly. Devices employed for cell capture and on-chip lysis were functionalized with a monoclonal CD4 antibody and primed with PBS containing 1% BSA and 1 mM EDTA, as previously described (Cheng, et al., Lab Chip, 2007, 7, 170-178.).

Cell Preparation and on-Chip Cell Isolation

Peripheral blood mononuclear cells (PBMCs) were prepared from freshly drawn blood through Ficoll density gradient centrifugation (Ferrante, et al., J. Immunol. Methods, 1980, 36, 109-117. English, et al., J. Immunol. Methods, 1974, 5, 249-252.), and maintained in RPMI-1640 medium. To isolate CD4+ T lymphocytes, PBMCs maintained in RPMI-1640 media were injected into anti-CD4 antibody functionalized microelectrode devices at a flow rate of 5 μL/min for different lengths of time, followed with rinsing unbound cells from the devices using PBS containing 1% BSA and 1 mM EDTA. The number of cells captured within the microfluidic devices was counted manually under a phase contrast microscope (Cheng, et al., Lab Chip, 2007, 7, 170-178.).

Off-Chip Sample Preparation for Impedance Measurement

To prepare cell lysates off-chip, cultured PBMCs were counted manually using a hemocytometer, then diluted with RPMI-1640 to different concentrations ranging from 0 to 3,500 cells/4 in eppendorf tubes, with a final volume of 1 mL. Afterwards, the cells were pelleted at 1200 g for 5 minutes and gently washed three times with 1 mL of low-conductive media (8.5% sucrose and 0.3% dextrose). After the final wash, the cells were resuspended in 1 mL sterilized deionised water and left to sit at room temperature for 20 minutes for cell lysis. Each cell lysate was then injected into the microelectrode devices starting from the lowest concentration at a flow rate of 15 μL/min, and impedance spectra were taken after signals were stable. The devices were rinsed with deionized water between lysate injections at a flow rate of 50 μL/min until the impedance measurement reached the original values for de-ionized water.

Optical Characterization of on-Chip Cell Lysis Using Sugar Solutions

To identify a low conductive media to lyse cells at a controlled rate, we diluted a low conductive viability-maintenance solution containing 8.5% sucrose and 0.3% dextrose to different final concentrations. These solutions were injected sequentially into microfluidic channels with captured CD4+ T lymphocytes using a syringe pump (Harvard Apparatus) at a flow rate of 15 μL/min for 1 min, and cells were allowed to lyse in each solution for 10 min. These cells were pre-stained using Fluo-3 and captured in microfluidic channels by surface-immobilized antibody using methods described previously (Cheng, et al., Lab Chip, 2007, 7, 170-178.). Fluorescent images were taken every 30 seconds throughout the course of the experiment, and the number of fluorescent cells were enumerated to estimate the number of intact cells.

On-Chip Preparation for Impedance Spectroscopy

To detect surface immobilized cells, ions present in PBS buffer were washed out of the channels using a low conductivity washing solution containing 8.5% sucrose and 0.3% dextrose, at a flow rate of 20 µL/min until impedance signals were stable. Next, a low-conductive cell lysing solution containing 2% sucrose and 0.07% dextrose was flowed in at a flow rate of 10 µL/min for 1 min for cell lysis. After the lysing solution was introduced, flow was stopped, and cells were kept in this solution for another 10 min to allow cell lysis to reach steady state. Following cell lysis, de-ionized water was injected at a flow rate of 20 µL/min for 5-10 minutes to acquire reference spectra. Impedance was monitored continuously throughout the entire process.

Impedance Spectroscopy Measurements

Impedance measurements were taken using an Agilent 4284 LCR meter (Agilent Technologies Inc., Palo Alto, Calif.). The microelectrode devices were connected to the LCR meter through platinum probes; a schematic of the experimental setup is shown in FIG. 1A. The impedance measurement process was automated by custom LabView (National Instruments Corp., Austin, Tex.) virtual instruments and GPI B interface. Impedance spectra were measured in the frequency range of 100 Hz to 1 MHz with a frequency increase factor of 1.5, and amplitude of 250 mV.

Results

All devices used in this study are composed of surface microelectrodes patterned within channels with the dimensions of 5 cm×4 mm×50 µm. When immobilized with specific antibody and operated under controlled flow conditions, this channel design has been shown previously to specifically isolate CD4+ T lymphocytes (purity >95%) with high efficiency (>90%) from unprocessed whole blood (Cheng, et al., Lab Chip, 2007, 7, 170-178.). In the current study, we further patterned microelectrodes in antibody-functionalized microchannels for the purpose of detecting isolated cells electrically. Using an appropriate electrode layout for on-chip cell lysis and counting (FIG. 1C), both isolation purity and yield remained above 90% for CD4+ T cell separation from whole blood, due to maintenance of 85% of affinity surface areas within the channels.

Impedance Measurement Using Off-Chip Cell Lysate

Figure 2:
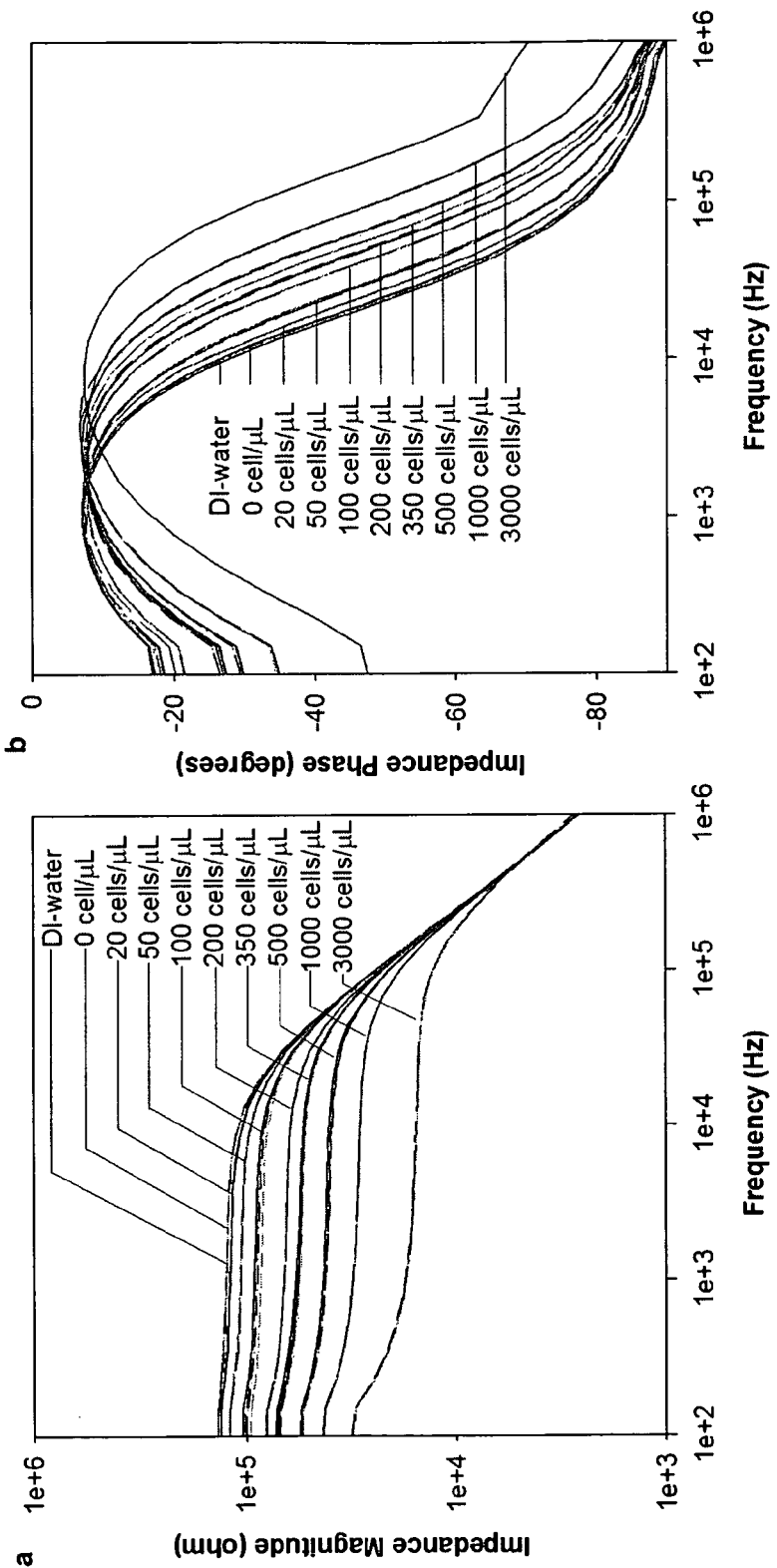
FIGS. 2A and 2B are graphs showing impedance spectra and impedance change as a function of cell concentration using cell lysate obtained off-chip. (A) Impedance magnitude and (B) phase spectra of DI water and cell lysate with different starting cell concentrations measured on the IDT device. Three to five scans were performed at each cell concentration in the frequency range between 100 and $10^6$ Hz.
FIG. 2C-2E are graphs showing impedance magnitude measured at 760 Hz plotted in log-log scale as a function of cell concentration using (C) top-bottom electrodes, (D) IDT electrodes and (E) two rail electrodes. The solid dots in (C)-(E) are experimental measurements that were fit to two-parameter power equations. The least square fits are shown as solid lines and equations in the graph. Error bars indicate the standard deviation from 3-5 continuous measurements within a single device.
Figure 2:
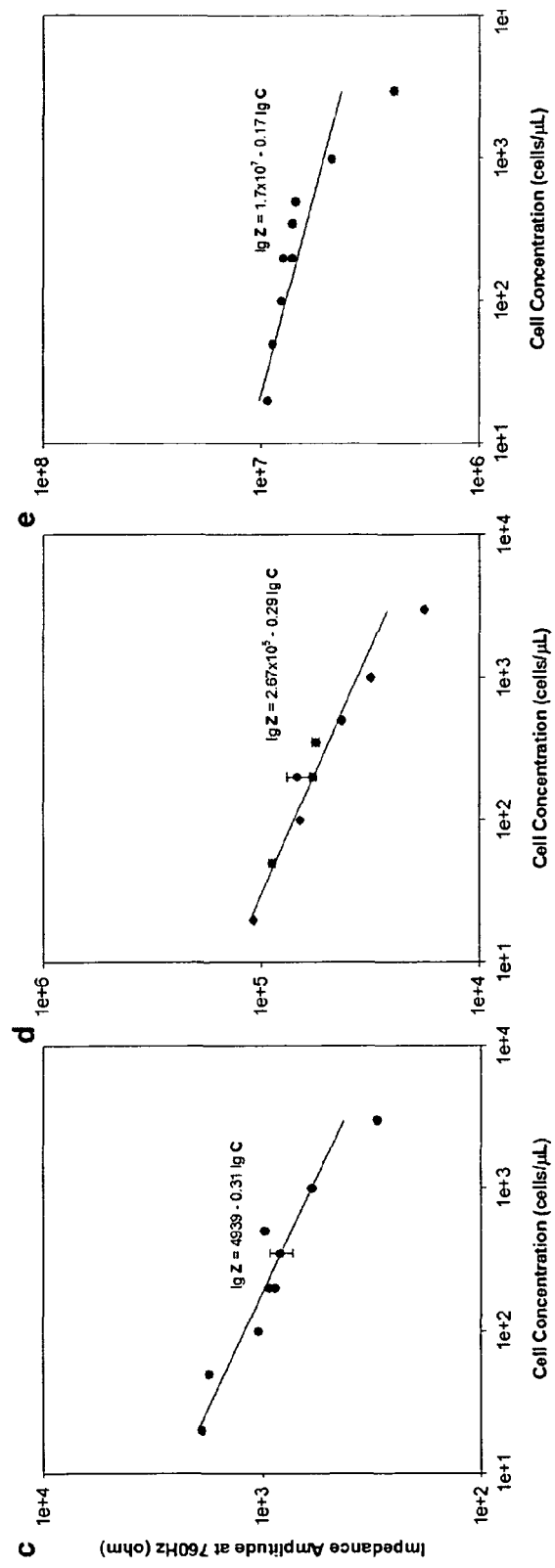

To test the detection sensitivity of ion release from primary cells using impedance spectroscopy, we first lysed PBMCs of known concentrations in eppendorf tubes with de-ionized water, and measured impedance of the lysate using microfluidic devices of three different electrode designs: top-bottom electrodes, IDT co-planar electrodes and simple two-rail co-planar electrodes. FIGS. 2A and 2B show the spectra of impedance magnitude and phase as a function of frequency for cell concentrations ranging from 0 to 3,000 cells/µL measured using the IDT electrodes. We observed that each magnitude spectrum has two regions, a constant impedance region in the frequency range from 100 Hz to 10 kHz, and a region of decreasing impedance at the higher frequency range (>100 kHz). With increasing cell concentrations, there is a consistent decrease in impedance magnitude in the low-frequency range, and a shift of phase peak to higher frequency. This suggests strongly that semi-quantitative measurement of cell concentrations can be determined using cell ion release. The impedance magnitude spectra obtained from the other two electrode designs demonstrated similar properties, but different absolute values; the impedance magnitude measured using two-rail electrodes are two orders of magnitude higher than those from the IDTs, which is another two orders of magnitude higher than the top-bottom electrodes. The transition point where impedance begins to drop on the magnitude spectra occurs around 10 kHz for the top-bottom electrodes, but shifted to around 1 kHz for the simple two-rail electrodes.

To examine the ability of the impedance spectra to discriminate cell concentrations, we plotted impedance magnitude at 760 kHz versus cell concentration for the three types of electrode designs (FIGS. 2C-2E). We chose 760 kHz as the measurement frequency due to the maximum separation of impedance magnitude at this frequency for all three electrodes. The response of impedance magnitude to cell concentration is linear in a log-log scale plot, similar to the relationship between the resistance of a simple electrolyte solution and solute concentration in the range relevant to our study (Omega Engineering, Technical Conductivity and Resistivity. Accessed: Dec. 30, 2006.). This indicates that the release of the ionic contents from cells and the subsequent conductance of the medium in which the cells are lysed are proportional to the number of cells. Moreover, using ion release to detect cells appears to be extremely sensitive, and can detect as few as twenty cells per microliter in a low conductive solution.

Impedance Modeling and Parameter Extraction

As cell ion release mainly contributes to bulk conductance change, we used the circuit model shown in FIG. 3A to fit both impedance magnitude and phase spectra using least square criteria in MATLAB, to extract bulk conductance values $G_{sol}=1/R_{sol}$. By iterating each of the initial conditions in the model, the least square error between the model and the experimental data was minimized, to a value of $10^{-13}$ or less (Vetter, Electrochemical kinetics: theoretical and experimental aspects, New York: Academic Press, 1967. Evgenij Barsoukov and J. R. Macdonald, eds., Impedance spectroscopy: theory, experiment, and applications, Hoboken, N.J.: Wiley-Interscience, c2005., 2005.). The fitting is then terminated, and the parameters are extracted and recorded.

FIGS. 3B and 3C show a typical fitting of the impedance magnitude and phase spectra using lysate from solutions containing 3,000 cells/µL: close match between the measurements (crosses) and fitting curves (solid lines) indicates that the selected circuit model predicts the experimental system well.

After extracting bulk conductance from all spectra, we plotted bulk solution conductance as a function of cell concentration (solid circles in FIGS. 3D-3F). With all three electrode designs, solution conductance increases linearly with the number of cells contributing to ion concentration, confirming our hypothesis that ion release and solution conductance change are proportional to cell number. We also observed that $R_{sol}$ values dominate impedance magnitude measurements in an intermediate frequency range between 100 to 10 kHz. This indicates that the bulk conductance can be estimated by measuring impedance magnitude at a single frequency using a simple hand-held setup, instead of an LCR meter.

Slopes of the conductance curves represent measurement sensitivity of each electrode design. We observed that top-bottom electrodes have the highest detection sensitivity ($9.18\times10^{-7}$/(ohm·cell)), while the simple two-rail electrodes have the lowest sensitivity ($9.92\times10^{-11}$/(ohm·cell)); the detection sensitivity of the IDT electrodes falls in between ($1.90\times10^{-8}$/(ohm·cell)). For easy visualization of cells within the microfluidic devices as well as sensitive detection of cell ion release, we chose the IDT electrodes for further cell capture and on-chip lysis experiments.

Optical Characterization of on-Chip Cell Lysis Using Hypotonic Sugar Solutions

After confirming the feasibility of detecting cells through their ion release using off-chip lysate and impedance spectroscopy, we were interested in testing this strategy to detect and quantify cells captured within microfluidic devices. To accomplish on-chip cell lysate impedance spectroscopy, we needed to first replace electrolyte-rich whole blood or saline buffer with a non-conductive, isotonic solution, to reduce background conductivity in the microfluidic channel and establish a baseline measurement. The off-chip experiments using DI water for cell lysis could not be applied directly to on-chip cell lysis, as cells suspended in DI water lyse immediately, and the lysate would be washed out of the chip prior to impedance measurements. Given the desire that the medium into which the cells are lysed be as non-conductive as possible, and the desire to wash away the ionic and protein content from the blood sample itself, we evaluated different low-conductive media as cell wash and cell stabilization solutions. We found that a sugar-based washing solution containing 8.5% sucrose and 0.3% dextrose satisfied the two criteria of ion removal and cell stabilization. Impedance of this solution is close to deionized water, but cell viability can be maintained for more than 60 minutes (Chiou, et al., Nature 2005, 436, 370-372.). Further dilutions of this solution with deionized water can be expected to decrease the solution osmolarity, so that lysing speed can be controlled by adjustments in the dilution factor.

Figure 4:
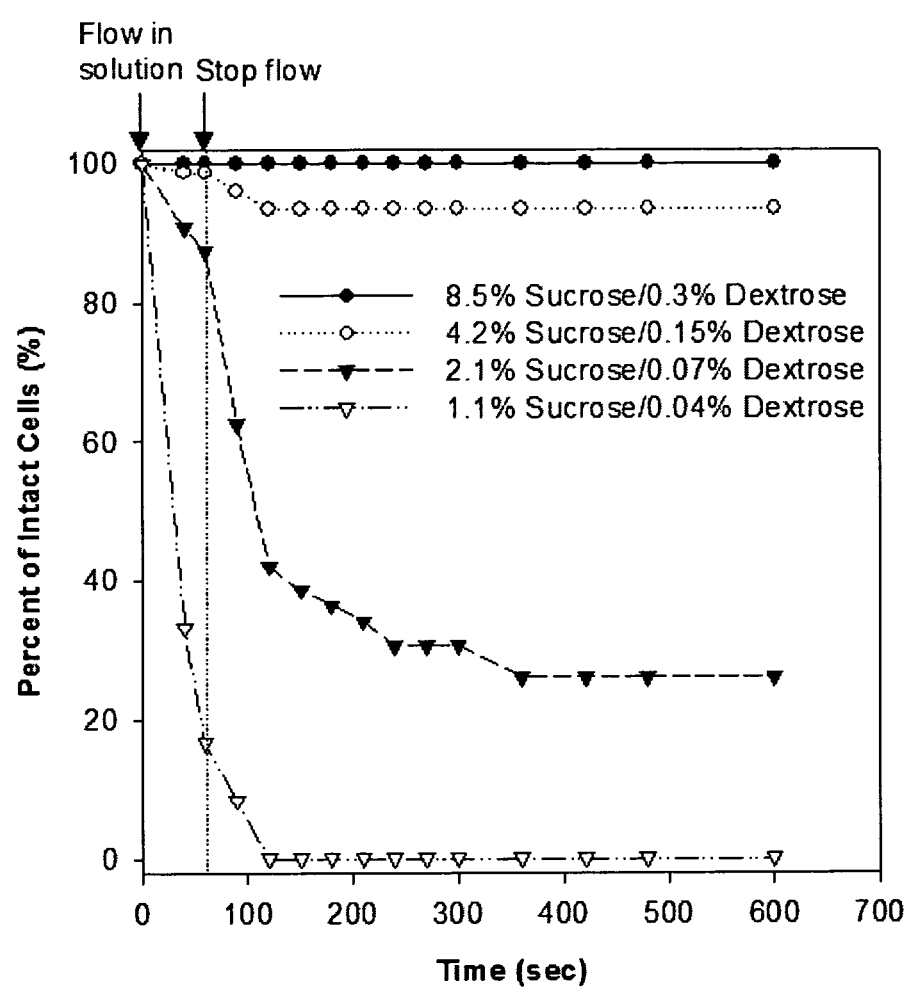
FIG. 4 is a graph showing percentage of viable cells as a function of time in different concentrations of low conductivity sugar solution observed under a fluorescence microscope. CD4+ T cells were captured in antibody-immobilized devices followed with flowing in sugar solutions of different concentrations at 10 mL/min for 2 min. After solution flow was stopped, cells were incubated at room temperature in this solution for 8 minutes, and the number of intact cells was counted under a fluorescent microscope every 30 seconds. The percentage of intact cells was calculated by dividing the number of intact cells by total number of cells before injection of each sugar solution.

To test lymphocyte viability and lysis in low-conductivity sugar solutions, we isolated CD4+ T lymphocytes from PBMCs within functionalized microchannels, as described (Cheng, et al., Lab Chip, 2007, 7, 170-178.). After washing off unbound cells, we introduced the low-conductive 8.5% sucrose/0.3% dextrose washing solution, as well as more hypotonic sugar solutions. After flow of the sugar solution was stopped, the number of intact cells on the imaged area (600 mm×800 mm) was counted every 30 seconds by fluorescence microscopy. FIG. 4 shows the percentage of viable cells versus time in the 8.5% sucrose/0.3% dextrose solution, and in different dilutions of this solution. Lymphocytes remain intact for at least 30 minutes in 8.5% sucrose/0.3% dextrose; lysis accelerates in more dilute sugar solutions. Based on these results, the 8.5% sucrose/0.3% dextrose solution was used as the initial wash solution, and a solution containing 2% sucrose and 0.07% dextrose was chosen for on-chip cell lysis. With this combination, we observed that up to 15% of captured cells lyse in the first minute of solution exchange, minimizing ion loss due to flow, while around 80% of cells are lysed within 10 minutes, making timely measurement possible.

Impedance Spectroscopy for on-Chip Cell Lysis

Figure 5:
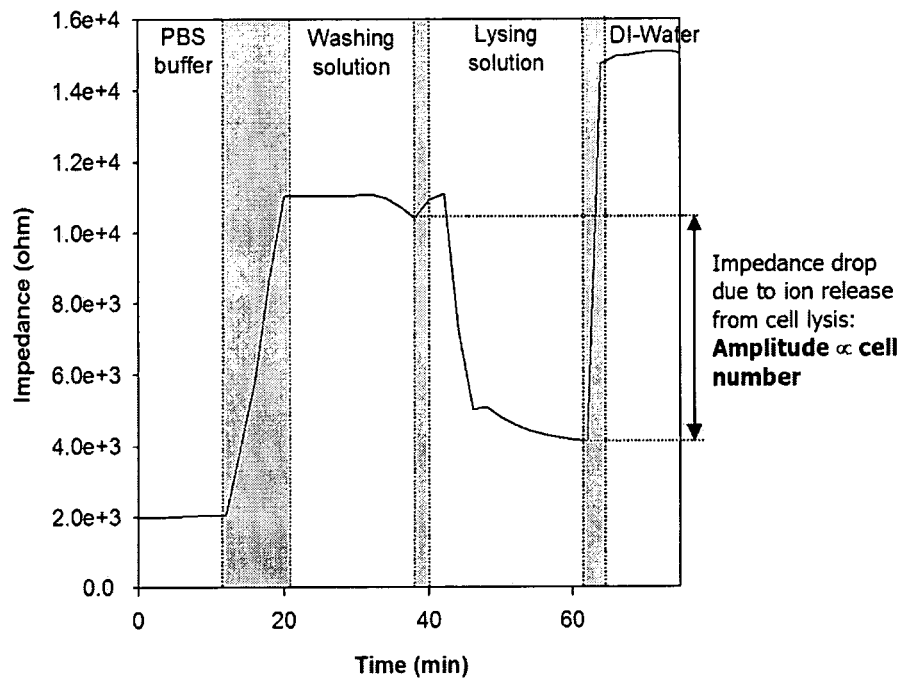
FIG. 5A is a graph showing impedance magnitude at 760 Hz during the process of cell capture and on-chip lysis. The respective incubation steps are labeled on top of the graph and the shaded areas between these labelled steps are transient states during solution exchanges. The impedance drop before and 10 minutes after injecting the lysing solution is associated with cell lysis and is used as a cell-number indicator.
FIG. 5B is a graph showing conductance change versus the number of cells captured within microfluidic devices. Bulk solution conductance was extracted from the impedance spectra, and conductance drop before and 10 minutes after flowing in the lysing solution was taken as the indicator to count cell. This conductance change increases proportionally with the number of cells captured within the microfluidic chip, suggesting immobilized cells can be counted by electrical measurement of their ion release. Nonlinearity of the relationship may arise from incomplete diffusion of ions within the measurement time. Each data point in the plot represents measurement from one device.
Figure 5:
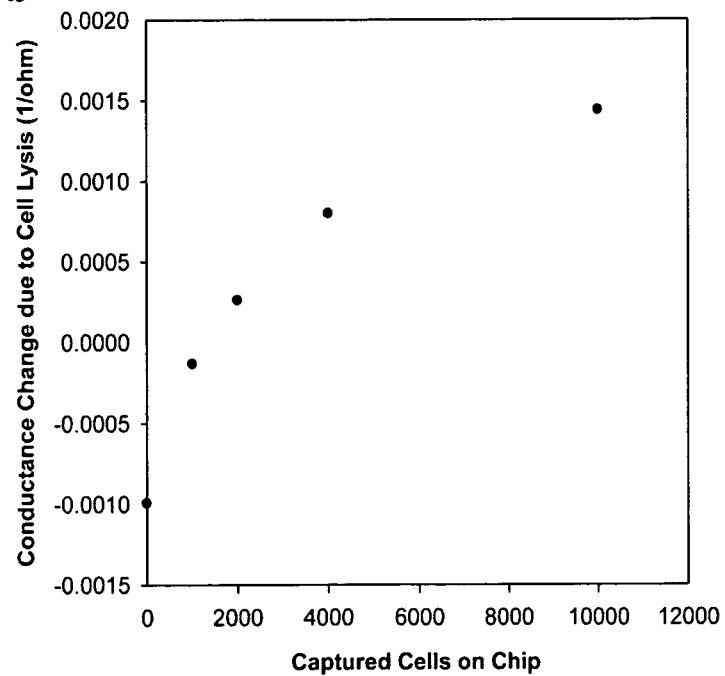

After optimizing the ion-free, low conductive solutions for cell washing and lysis, we next measured impedance changes after on-chip cell capture and cell lysis. CD4+ T cells were captured from culture media, rinsed with PBS buffer, rinsed again with the isotonic 8.5% sucrose/0.3% dextrose solution. After measurements of impedance baselines, the low conductivity cell lysing solution (2% sucrose/0.07% dextrose) was introduced into the microfluidic devices, and cells were allowed to lyse for 10 minutes. Reference spectra were obtained with de-ionized water. Throughout the experiment, impedance spectra were acquired continuously. However, impedance measurements at a single frequency between 100 to 10,000 Hz reflected very well changes of the solution electrical property arising from cell lysis. For example, FIG. 5A shows the typical change of impedance magnitude acquired at the frequency of 760 Hz before and after on-chip cell lysis. Impedance magnitude remains in the low kilo-ohm range when cells are in PBS, due to the high ionic concentration of saline buffers. Impedance increases dramatically to above ten kilo-ohms upon introduction of the low-conductive 8.5% sucrose/0.3% dextrose washing solution. When cells are kept in the washing solution in a static state, impedance magnitude decreases slightly, likely due to low-level cell ion release in a hypo-osmotic environment. After injection of the ion-free 2% sucrose/0.07% dextrose lysing solution, we noticed an initial impedance jump. This was followed by an abrupt drop of impedance and a subsequent slower impedance decrease. This two-phase impedance drop during cell lysis matches optical observation of cell lysis in the same solution (FIG. 4), suggesting that the decrease of impedance magnitude arises from lysis of the captured cells.

Following application of the fitting procedure described above, we extracted bulk conductance from the impedance spectra and the conductance change before and 10 minutes after introduction of the lysing solution. When we compare this conductance change to manual cell counts within the microfluidic devices (FIG. 5B), it is evident that bulk conductance changes is proportional to the number of captured cells contributing to ions. This successfully demonstrates that cells can be detected and counted within a microfluidic device through electrical measurement of the impedance and conductance of cell lysate.

Discussion

We describe here a method to detect and quantify immobilized cells in a microfluidic device through bulk electrical measurements based on cell ion release using impedance spectroscopy. We selected CD4+ T lymphocytes as the target cells for detection due to their clinical significance for the management of HIV infected patients (Department of Health and Human Services (Oct. 6, 2005) Guidelines for the Use of Antiretroviral Agents in HIV-1-Infected Adults and Adolescents. Accessed 20 Mar. 2006.). The most immediate use of a microfluidic CD4 counter would be to differentiate the CD4 threshold of 200 cells/μL for treatment decisions (Centers for Disease Control and Prevention Revised classification for HIV infection and expanded surveillance case definition for AIDS among adolescents and adults in MMWR Morbidity and Mortality Weekly Report 1-19 (1992). World Health Organization (4 Nov. 2005) Patient Monitoring Guidelines for HIV Care and ART. Accessed 20 Mar. 2006.). The detection limit of cell lysate impedance spectroscopy clearly meets this requirement and shows promise in the development of microfluidic CD4 count diagnostic tools that can be used at the point of care. In addition, this cell counting strategy is not limited to the detection of blood cells, but can be applied to any biological target with rich ion content. To our knowledge, capability to isolate and detect 1 cell on a millimeter square size area, or to detect 20 cells in a microliter volume, represents the most sensitive approach to enumerate immobilized cells using non-optical method.

Microchip devices used in the current study are composed of surface patterned microelectrodes fabricated within a microfluidic channel. The microchannel walls are functionalized with a monoclonal anti-CD4 antibody and the electrodes are passivated using bovine serum albumin. The channel design and sample flow conditions are selected to ensure specific isolation of CD4+ T lymphocytes from whole blood with high efficiency, as described previously (Cheng, et al., Lab Chip, 2007, 7, 170-178.). With appropriate electrode layout for on-chip cell lysis and counting (FIG. 1C), both isolation purity and yield remain above 90% from whole blood, due to maintenance of >85% of the affinity surface areas. Very few cells attach non-specifically on the electrode surfaces when observed under an optical microscope, demonstrating expected device performance for cell isolation.

The separated cells are further detected by complete cell lysis and bulk conductance measurements using surface electrodes. As an effort to identify the frequency range that yields the best detection sensitivity, we acquired impedance magnitude and phase spectra as a function of frequency in this study, and fit the spectra to a circuit model to extract bulk conductance. With the knowledge of optimal frequency range (between 100 and 10,000 Hz in FIG. 2A) and the observation that $R_{sol}$ values dominate impedance magnitude at these frequencies, one can estimate bulk conductance in seconds by monitoring impedance magnitude at a single frequency (e.g., 760 Hz) using a hand-held setup. Thus, the whole process from cell capture to cell lysis and detection could be accomplished in less than 10 minutes.

Specifically, for detection and monitoring of CD4 cells in HIV-infected patients, 200 cells per μL is used as a clinical decision point. We show here that integration of a immunoaffinity cell capture approach with an electrical detection method can meet this detection threshold. The microfluidic device we describe is capable of isolating specific cell types from blood and quantifying cell number, and can serve as a single-use cartridge for a hand-held instrument to provide simple, fast and affordable cell counting in point-of-care settings.

The ability to detect cells electrically, as opposed to optically, presents the following key advantages: (i) label-free detection, (ii) automatability, and amenability to the development of a small table top or handheld instrument, (iii) integratability with microfluidic devices; and (iv) sensitivity of detection in a physiologically and clinically relevant range of cell concentrations. Compared to other electrical approaches to counting cells, cell lysate impedance spectroscopy demonstrates a few orders of magnitude improvement in detection sensitivity. This is due to the reduced background conductance when cells are stabilized in an ion-free, low conductivity sugar solution and rich ion content released from mammalian cells upon hypotonic lysis. Changes in solution conductance in the process of cell lysis are extracted from the spectra of impedance measurements. We demonstrate that bulk conductance of cell lysate is proportional to the original cell number, which forms the basis of cell lysate impedance spectroscopy. This method is sensitive enough to detect as low as twenty cells per microliter in a device with a volume of 10 μL and a footprint of 2 cm$^2$, which represents <10$^{-4}$ volume replacement and <10$^{-4}$ surface coverage.

To measure bulk conductance in a microfluidic device, we patterned surface electrodes within microchannels and modeled impedance spectra using a simple circuit, which contains a dielectric capacitance ($C_{di}$) in parallel with the sum of bulk solution resistance ($R_{sol}$) and interfacial impedance ($Z_{dl}$). From experimental fitting, we observe that the magnitude of $Z_{dl}$ is generally much smaller than the solution resistance $R_{sol}$. As a result, $R_{sol}$ dominates the circuit at the low frequency range (<1-10 kHz depending on electrode geometry), leading to relatively constant impedance, independent of frequency change. Dominance of $R_{sol}$ in the low frequency range is also observed as humps in the phase spectra. As ionic concentration of the solution increases, bulk solution resistance decreases, shifting the range where $R_{sol}$ dominates to higher frequencies, and decreasing the overall impedance in that same range. In the high frequency range (10-100 kHz), on the other hand, dielectric capacitor ($C_{di}$) dominates, resulting in impedance magnitude drop with frequency increase. At even higher frequencies (>100 kHz), inductance of the electrochemical device and connecting wires all contribute to the impedance spectra, resulting in merging of all the impedance curves regardless of solution conductivity (Katz, et al., Electroanalysis, 2003, 15, 913-947.).

Monitoring biological ion release using impedance spectroscopy in a micro-device is a well established technique to study metabolism and growth of micro-organisms (Gomez-Sjoberg, et al., J. Microelectromech. Syst., 2005, 14, 829-838. Gomez, et al., Sens. Actuator B-Chem., 2002, 86, 198-208.). However, similar approaches have not been reported previously for mammalian cells, likely due to their intolerance to an ion-free environment, which is required to reduce background conductance for sensitive measurement of ions released by cells. We demonstrate here the possibility to maintain the viability of primary cells in an ion-free sugar solution and the feasibility to measure bulk conductance change due to cell ion release through impedance spectroscopy. This strategy differs in principle from other non-optical strategies to detect adherent cells, such as surface impedance spectroscopy, field effect sensors and mechanical cantilevers (Koch, et al., J. Micromech. Microeng., 1999, 9, 159-161. Ehret, et al., Biosens. Bioelectron., 1997, 12, 29-41. Fromherz, et al., Science, 1991, 252, 1290-1293. Bull, et al., Am. J. Clin. Pathol., 1965, 44, 678-&. Tiruppathi, et al., Proc. Natl. Acad. Sci. U.S.A., 1992, 89, 7919-7923. Giaever, et al., Proc. Natl. Acad. Sci. U. S. A., 1991, 88, 7896-7900.). These approaches are based on detecting differences between the electrical or physical properties of cells and the surrounding medium. This difference is generally small; thus the characteristic sensing elements and the target entity are usually of comparable dimensions for sensitive detection, unless the differences are manually enhanced (Katz, et al., Electroanalysis, 2004, 16, 19-44. Wang, Anal. Chim. Acta, 2003, 500, 247-257.). In contrast, in our approach, the electrical signal is amplified by taking advantage of the large amount of ions pre-existing inside the target cells. This allows for sensitive detection of cells with very low surface coverage or volume replacement, without significant additional manipulation.

Another advantage of our strategy is the flexibility in sensor design. The possibility to sensitively measure bulk impedance using simple two rail, co-planar electrodes or top-bottom electrodes indicate one could use simple metal plates or wires to implement our approach with less sophisticated technologies without sacrificing the detection limit. When the three electrode geometries are compared, the top-bottom electrodes demonstrated the highest detection sensitivity, while simple two rail electrodes have the lowest detection sensitivity. Assuming solution in the fluidic channel is a simple conductor, theoretical conductance measured at each condition can be calculated using the following equation:

$$G = \sigma m A/L \quad (2)$$

where σ is the solution conductivity, A is the solution cross-sectional areas between the electrodes, L is the spacing between electrodes and m is the electrode repeats. Since solution conductivity is independent of the device design, this geometrical factor essentially determines measurement sensitivity. When the geometrical factor (m A/L) is calculated for the three electrode designs used in this study, we obtain values of 400, 150 and 0.065 cm for the top-bottom, IDT and simple electrodes, respectively. This order of geometrical factor matches our measurement sensitivity from the conductance plots (FIG. 3d-3f). However, when we calculate theoretical conductance using Eq. 2 by assuming each cell releases 10$^{-14}$ molar ions after complete lysis, the predicted conductance is one to three orders of magnitude higher than measurements obtained using off-chip lysate, indicating ions in the bulk do not contribute to conduction to the same level. In fact, DeSilva et. al. have hypothesized that electrical conductance through in-plane electrode islands bridged with immobilized proteins was dominated by ion conduction of hydrated protein layers (Desilva, et al., Biosens. Bioelectron., 1995, 10, 675-682.). Applying their model to our system, the dominating conductive layer could be close to the substrate and is much thinner than the channel dimensions, explaining the deviation between measurements and calculated conductance using Eq. 2. When impedance magnitude is compared between on-chip and off-chip lysing experiments using IDT electrodes, we also observed an order of magnitude difference. This difference may be accounted for by separate preparations of these two types of devices: devices used for the off-chip lysate experiments were not subjected to surface modification, while those for on-chip lysis contain multiple layers of chemicals and proteins in the gap between the electrodes, changing the electrical properties of the gaps. In addition, electrodes used for on-chip lysis experiments are primed with albumin, which is likely to alter electron transfer kinetics and ion diffusion characteristics on the electrode (Katz, et al., Electroanalysis, 2003, 15, 913-947.). Despite the difference in absolute impedance magnitude between these two types of devices, measurement taken using devices under the same preparation clearly demonstrate comparable performance, as observed with reference solution spectra.

An interesting observation noted is the slight impedance drop when keeping cells in the low-conductive washing solution. This may indicate the release of ions from captured cells despite an intact morphology under optical microscopy. As the washing solution is slightly hypo-osmotic (270 mOsm), cells are likely to swell when they are first exposed to the washing solution. Transient osmotic swelling and the following regulatory volume decrease (RVD) are known to cause KCl efflux induced by parallel activation of $K^+$ and $Cl^-$ channels (Pedersen, et al., Comp. Biochem. Physiol. A-Mol. Integr. Physiol., 2001, 130, 385-399. Okada, et al., J. Physiol.-London, 2001, 532, 3-16. Pasantes-Morales, et al., Neurochem. Res., 2000, 25, 1301-1314. Charras, et al., Nature 2005, 435, 365-369.), which can result in the observed solution conductance decrease. This observation suggests it is possible to directly study cell response to a hypotonic solution and RVD using electrical approaches. Such measurements could provide better sensitivity compared to conventional methods based on optical measurements of cell sizes, which are low throughput and prone to measurement errors. Cell ion release and volume adjustment in response to changes in environmental osmolarity may also explain the heterogeneous cell lysis as observed in FIG. 4. Since memory and native T cells have been reported to contain different ion stores (Sigova, et al., FEBS Lett., 1999, 447, 34-38.), it is not surprising that these cells may have different capability to adjust to hypo-osmotic conditions, and demonstrate different lysing speed.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of counting mammalian cells in a sample, the method comprising:
    introducing the sample into a channel, wherein a surface of the channel is coated with binding moieties that bind specifically to a cell surface marker of the mammalian cells;
    immobilizing the mammalian cells in the channel by allowing the mammalian cells to bind to the binding moieties;
    introducing an isotonic, low conductivity solution into the channel to reduce background conductivity in the channel;
    measuring an impedance baseline in the channel;
    lysing the cells in the channel by replacing the isotonic, low conductivity solution in the channel with a hypotonic, low conductivity solution; and
    measuring an impedance in the channel after cell lysis, a change in impedance from the impedance baseline is indicative of the number of mammalian cells lysed in the channel.

2. The method of claim 1, wherein measuring the impedance baseline and the impedance in the channel after cell lysis both comprise applying an electric field to the channel at a single frequency between about 100 Hz and about 10 kHz.

3. The method of claim 1, wherein the change in impedance occurs as a result of a release of intracellular ions from the mammalian cells as a result of the lysing.

4. The method of claim 1, wherein the change in impedance occurs as a result of a release of nuclei from the mammalian cells as a result of the lysing.

5. The method of claim 1, wherein measuring the impedance baseline and the impedance in the channel after cell lysis both comprise using an electrode selected from the group consisting of: a top down electrode, an interdigitated (IDT) electrode, and a two rail electrode.

6. The method of claim 1, wherein the mammalian cells comprise CD4+ lymphocytes and the binding moieties comprise anti-CD4 antibodies.

7. The method of claim 1, wherein the sample comprises a heterogeneous mixture of cells.

8. The method of claim 7, wherein the sample is blood.

9. The method of claim 1, wherein the isotonic, low conductivity solution comprises about 8.5% sucrose and about 0.3% dextrose.

10. The method of claim 1, wherein the hypotonic, low conductivity solution comprises about 2% sucrose and about 0.07% dextrose.

11. The method of claim 1, wherein the hypotonic, low conductivity solution comprises a detergent.

12. The method of claim 1, wherein the channel is a closed microfluidic channel.

13. The method of claim 1, wherein a change in impedance between the impedance baseline and the impedance in the channel after cell lysis is caused by a change in bulk conductivity of the sample in the channel.

14. The method of claim 1, wherein an impedance of the isotonic, low-conductivity solution is greater than 1 k$\Omega$.

15. The method of claim 1, wherein an impedance of the isotonic, low-conductivity solution is greater than 10 k$\Omega$.

16. The method of claim 1, wherein an impedance of the isotonic, low-conductivity solution is greater than 1 M$\Omega$.

* * * * *

UNITED STATES PATENT AND TRADEMARK OFFICE
CERTIFICATE OF CORRECTION

PATENT NO. : 8,852,875 B2  Page 1 of 1
APPLICATION NO. : 12/596768
DATED : October 7, 2014
INVENTOR(S) : Mehmet Toner et al.

It is certified that error appears in the above-identified patent and that said Letters Patent is hereby corrected as shown below:

Title Page, Column 2, line 3 Other Publications:

Delete "electropermeabilizatiion" and Insert --electropermeabilization--

Signed and Sealed this
Twenty-fourth Day of February, 2015

Michelle K. Lee
*Deputy Director of the United States Patent and Trademark Office*